United States Patent [19]

Yang et al.

[11] Patent Number: 4,906,728
[45] Date of Patent: Mar. 6, 1990

[54] ACETAL COPOLYMERS WITH BACKBONE BROMO FUNCTIONAL GROUPS

[75] Inventors: Nan-Loh Yang, Staten Island, N.Y.; Andrew Auerbach, Livingston; James L. Paul, Summit, both of N.J.; Rose Pesce, College Point; Shian S. Wang, New York, both of N.Y.

[73] Assignee: Hoechst Celanese Corp., Chatham, N.J.

[21] Appl. No.: 181,237

[22] Filed: Apr. 13, 1988

[51] Int. Cl.$^4$ .................................................. C08G 4/00
[52] U.S. Cl. ..................................... 528/249; 528/244; 528/392
[58] Field of Search ................................. 528/249, 244

[56] References Cited

U.S. PATENT DOCUMENTS 3,297,647 1/1967 Schott ..................................... 260/73
3,337,587 8/1967 Tinsley et al. ....................... 260/338

FOREIGN PATENT DOCUMENTS 720516 10/1965 Canada ................................. 528/249
1196374 7/1965 Fed. Rep. of Germany ...... 528/249
2062958 7/1971 Fed. Rep. of Germany ...... 528/249

OTHER PUBLICATIONS

K. C. Brannock et al., J. Organic Chem. 21, 1366–1368 (1956).
R. C. Schulz, Makromol. Chem. Suppl. 12, 1–9 (1985).
R. C. Schulz, Makromol. Chem. Suppl. 13, 123–136 (1985).
P. H. Plesch and P. H. Westermann, Polymer, 10:105 (1965).
E. J. Vandenberg, J. of Polymer Sci. Polymer of Chem. Ed., 23:951–970 (1985).
S. Penszek, et al., Adv. Polymer Sci. 68/69, Cationic Ring Opening Polymerization, 2. Synthetic Applications, p. 91 (1981).

*Primary Examiner*—Harold D. Anderson
*Attorney, Agent, or Firm*—Dimitrios T. Drivas

[57] ABSTRACT

The invention concerns a method for producing an acetal copolymer containing backbone bromo-functional groups comprising copolymerizing trioxane with 5,6,-dibromo-1,3-dioxepene. The invention also concerns methods of modifying acetal copolymers containing bromo-functional groups and the copolymers produced by the methods of the invention.

6 Claims, No Drawings

ACETAL COPOLYMERS WITH BACKBONE BROMO FUNCTIONAL GROUPS

BACKGROUND OF THE INVENTION

Polyacetal copolymers are technically important macromolecules competitive with metals, ceramics and nylons in many applications. In the current technical processes, they are prepared by copolymerization of trioxane with a comonomer such as ethylene oxide, dioxolane or butanediol formal. Each such copolymer molecule carries a maximum of two functional groups, e.g. hydroxyl end groups. For purposes such as the preparation of graft copolymers and polymers with chemically bound stabilizers, it is desirable to synthesize polyacetals with higher levels of functional groups. It is an object of this invention to prepare polyacetal copolymers of trioxane that have stability equivalent to or greater than that of conventional resins while at the same time having functional groups which may be useful for further modifications or the attachment of additives.

In conventional acetal resin products, additives such as amidine thermal stabilizers and the like tend to reside in the amorphous regions of the polymer. Since the distribution of such non-crystalline areas is spatially random, the distribution of additives is often not optimal in terms of macroscopic properties. If functional sites can be provided at regular or semi-regular intervals (e.g. random copolymer) such that stabilizers or impact modifiers could be attached at a predetermined locus of points within the resin, then superior and more uniform properties could be achieved. This approach is particularly advantageous since the crystal structure of polyacetal is such that additives may be sterically obstructed from the crystalline areas. It therefore may be desirable to provide polymer backbone moieties that may disrupt the polymer's crystal structure in a controlled manner and provide a locus for attachment of additives.

Polyacetal copolymers with such backbone functional groups would be useful in many important applications such as: (a) preparing trioxane copolymers with chemically bonded stabilizers; (b) preparing trioxane copolymers with chemically attached impact modifiers; (c) preparing grafted copolymers of trioxane as compatibilizers with existing commercial acetal copolymer blends or with other polymer materials such as glass or minerals; (d) preparing copolymers amenable to surface modifications; and (e) preparing crosslinked copolymers.

SUMMARY OF THE INVENTION

The present invention concerns a method for producing an acetal copolymer container backbone halogen functional groups. A preferred embodiment concerns a method for producing a copolymer containing bromofunctional groups comprising copolymerizing trioxane with 5,6,-dibromo-1,3-dioxepene.

The invention also concerns the acetal copolymers produced by this novel method and the further modifications of these copolymers.

DETAILED DESCRIPTION OF THE INVENTION

EXAMPLE 1

(a) Synthesis of monomers

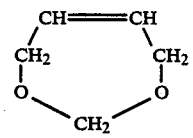

1,3-dioxep-5-ene, DXPE

A mixture of 176 g. (2 moles) of cis-2-butene-1,4-diol, 60 g (2 moles) of paraformaldehyde, 25 ml. of benzene and 0.25 g. of p-toluenesulfonic acid was refluxed under a Dean-Stark trap until the removal of water was completed. Distillation of the reaction mixture after the removal of benzene yielded 172 g. of crude 1,3-dioxep-5-ene (b.p. 120°-126° C.). The crude product containing small amounts of water and formaldehyde was purified by redistillation from solid potassium hydroxide. Pure 1,3-dioxep-5-ene (b.p.=130° C.) was obtained in the amount of 160 g.

EXAMPLE 2

5,6-dibromo-1,3-dioxepane

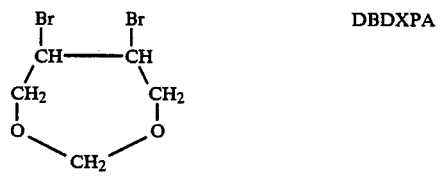

A solution of 15.2 g. (0.15 mole) of 1,3-dioxep-5-ene in 20 ml of carbon tetrachloride was cooled in an ice bath. A solution of 24 g. (0.15 mole) of bromine in 20 ml. of $CCl_4$ was then added dropwise with stirring. The solvent then was removed by distillation and the residue was recrystallized from ethanol to give 8.1 g. of 5,6-dibromo-1,3-dioxepane, m.p. 37° C.

EXAMPLE 3

(b) Copolymerization of Trioxane with 5,6-Dibromo-1,3-dioxepane

In a dry flask (Kjeldahl, 100 ml.) were placed 10 g. of trioxane and 2.5 g. of 5,6-dibromo-1,3-dioxepane. The flask was capped with a serum stopper. After removing the air and the dissolved gas under a vacuum from the reaction mixture, the flask was flushed with nitrogen. The contents were melted and mixed together with a magnetic stirrer in an oil bath (60°-65° C.). A volume of 0.2 ul. (microliters) of borontrifluoride etherate was then injected through serum stopper into the flask. The color of the solution changed from brown to white. Within about thirty minutes the solution became immobilized by the growth of the polymer throughout the flask. The reaction was allowed to proceed at 60° C. for 20 hours. At the conclusion of the polymerization, the polymer was removed and ground into small chunks. The crude polymer (9.5 gm) was first washed with 10 ml of a solution of methanol and 2% triethanolamine and then with methanol three times. The copolymer was dried under vacuum at 40° C. (9 gm).

This copolymer generates free radical readily upon u.v. irradiation as indicated by electron spin resonance absorptions. This photosensitivity may be useful for photochemical modifications of the polymer, e.g. surface grafting. The invention also contemplates the production of comonomers modified with other halogens such as chlorine. Acetal copolymers of trioxane containing backbone halogen functions grops such as chlorine can also be produced according to the methods of the invention. The sensitivity of the bromine and chlorine atoms toward ultraviolent light and high energy irradiation combined with the unzipping nature of the acetal copolymer itself may make the halogen modified copolymers of this invention useful as photoresists for application in intergrated circuits.

What is claimed is:

1. A method for producing an acetal copolymer containing pendent halogen functional groups comprising copolymerizing trioxane with a compound of the formula

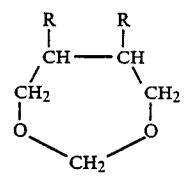

wherein R is a halogen.

2. The acetal copolymer produced by the method of claim 1.

3. A method for producing an acetal copolymer containing pendent bromofunctional groups comprising copolymerizing trioxane with 5,6-dibromo-1,3-dioxepane.

4. The acetal copolymer produced by the method of claim 3.

5. The method of claim 1 wherein R is bromine.

6. The acetal copolymer produced by the method of claim 5.

* * * * *